US00PP32685P2

(12) United States Plant Patent
Beekenkamp

(10) Patent No.: US PP32,685 P2
(45) Date of Patent: Dec. 22, 2020

(54) ***BEGONIA* PLANT NAMED 'BKPBEMCRS'**

(50) Latin Name: ***Begonia* x *hiemalis***
Varietal Denomination: BKPBEMCRS

(71) Applicant: Annie Cornelia Beekenkamp, Maasdijk (NL)

(72) Inventor: Annie Cornelia Beekenkamp, Maasdijk (NL)

(73) Assignee: BEEKENKAMP PLANTS B.V., Maasdijk (NL)

( * ) Notice: Subject to any disclaimer, the term of this patent is extended or adjusted under 35 U.S.C. 154(b) by 0 days.

(21) Appl. No.: 16/873,390

(22) Filed: Apr. 4, 2020

(51) Int. Cl.
*A01H 5/02* (2018.01)
*A01H 6/18* (2018.01)

(52) U.S. Cl.
USPC ..... Plt./348
CPC ..... *A01H 6/185* (2018.05)

(58) Field of Classification Search
USPC ..... Plt./348
CPC ..... A01H 6/185; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Begonia* plant named 'BKPBEMCRS', characterized by its broadly upright and mounded plant habit; sturdy plants with freely basal branching habit; dark green-colored leaves; uniform and freely flowering habit; and single flowers that are light red purple in color.

2 Drawing Sheets

Figure 1:
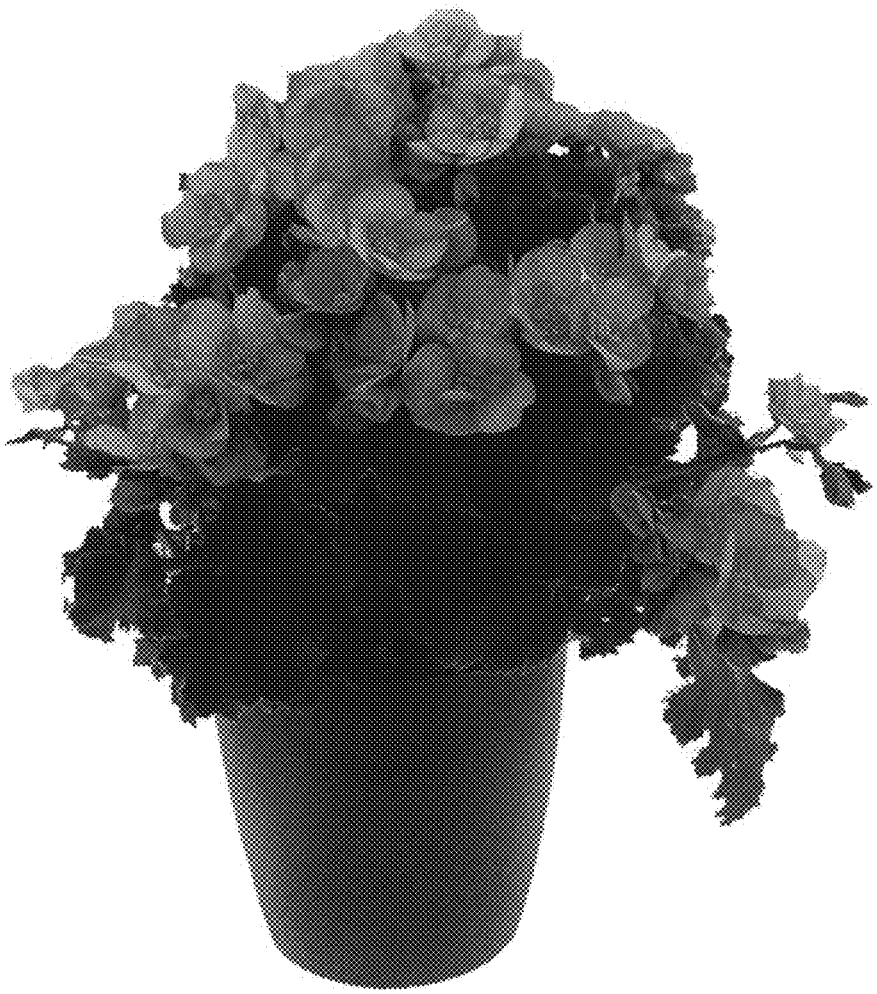

Botanical designation: *Begonia* x *hiemalis*.
Cultivar denomination: 'BKPBEMCRS'.

BACKGROUND OF THE INVENTION

The present invention relates to a new and distinct cultivar of *Begonia* plant, botanically known as *Begonia* x *hiemalis*, commercially referred to as Elatior *Begonia* and hereinafter referred to by the name 'BKPBEMCRS'.

The new *Begonia* plant is a product of a planned breeding program conducted by the Inventor in Maasdijk, The Netherlands. The objective of the breeding program was to develop new freely branching and freely flowering *Begonia* plants with attractive flowers and good garden performance.

The new *Begonia* plant originated from a cross-pollination made by the Inventor in September, 2013 of a proprietary selection of *Begonia* x *tuberhybrida* identified as code number 09-0008-06, not patented, as the female, or seed, parent with an unnamed proprietary selection of *Begonia socotrana*, not patented, as the male, or pollen, parent. The new *Begonia* plant was discovered and selected by the Inventor as a single flowering plant from within the progeny of the stated cross-pollination in a controlled greenhouse environment in Maasdijk, The Netherlands in July, 2014.

Asexual reproduction of the new *Begonia* plant by vegetative tip cuttings in a controlled greenhouse environment in Maasdijk, The Netherlands since September, 2014 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'BKPBEMCRS'. These characteristics in combination distinguish 'BKPBEMCRS' as a new and distinct *Begonia* plant:

1. Broadly upright and mounded plant habit.
2. Sturdy plants with freely basal branching habit.
3. Dark green-colored leaves.
4. Uniform and freely flowering habit.
5. Single flowers that are light red purple in color.

Plants of the new *Begonia* can be compared to plants of the female parent selection. Plants of the new *Begonia* differ primarily from plants of the female parent selection in the following characteristics:

1. Plants of the new *Begonia* have single-type flowers whereas plants of the female parent selection have semi-double-type flowers.
2. Plants of the new *Begonia* have light red purple-colored flowers whereas plants of the female parent selection have salmon pink-colored flowers.

Plants of the new *Begonia* can be compared to plants of the male parent selection. Plants of the new *Begonia* differ primarily from plants of the male parent selection in the following characteristics:

1. Plants of the new *Begonia* have larger flowers than plants of the male parent selection.
2. Flowers of plants of the new *Begonia* do not produce pollen whereas flowers of plants of the male parent selection produce pollen.

Plants of the new *Begonia* can be compared to plants of *Begonia* x *hiemalis* 'BKPBECRM', disclosed in U.S. Plant Pat. No. 28,818. Plants of the new *Begonia* differ primarily from plants of 'BKPBECRM' in the following characteristics:

1. Plants of the new *Begonia* are denser than and not as open as plants of 'BKPBECRM'.
2. Plants of the new *Begonia* have single-type flowers whereas plants of 'BKPBECRM' have double-type flowers.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet (FIG. 1 of 2) comprises a side perspective view of a typical flowering plant of 'BKPBEMCRS' grown in a container.

Figure 2:
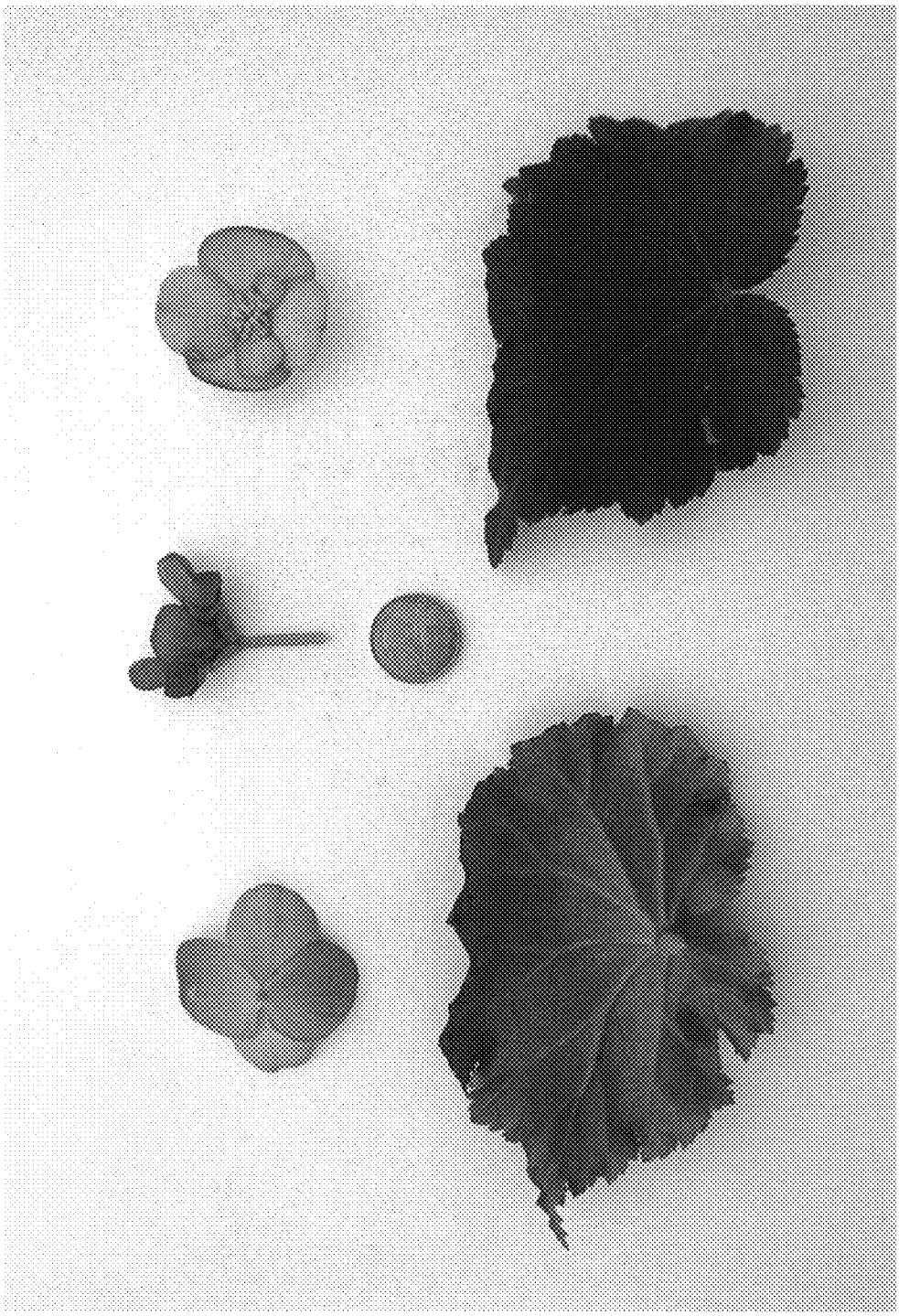

The photograph on the second sheet (FIG. 2 of 2) are close-up views of a typical flower bud and the upper and lower surfaces of typical developed flowers and leaves of 'BKPBEMCRS'.

DETAILED BOTANICAL DESCRIPTION

Plants used for the aforementioned photographs and following observations and measurements were grown during the summer in 10.5-cm containers in a glass-covered greenhouse in Dinslaken, Germany. During the production of the plants, day and night temperatures ranged from 19° to 21° C. Plants were eleven weeks from planting rooted cuttings when the photographs and the description were taken. In the following description, color references are made to The Royal Horticultural Society Colour Chart, 2015 Edition, except where general terms of ordinary dictionary significance are used.

Botanical classification: *Begonia* x *hiemalis* 'BKPBEMCRS'.

Parentage:

*Female, or seed, parent*.—Proprietary selection of *Begonia* x *tuberhybrida* identified as code number 09-0008-06, not patented.

*Male, or pollen, parent*.—Unnamed proprietary selection of *Begonia socotrana*, not patented.

Propagation:

*Type*.—By vegetative tip cuttings.

*Time to initiate roots*.—About 20 days at temperatures about 25° C.

*Time to produce a rooted young plant*.—About 35 to 36 days at temperatures about 21° C. to 23° C.

*Root description*.—Fine, fibrous; typically brown in color, actual color of the roots is dependent on substrate composition, water quality, fertilizer type and formulation, substrate temperature and physiological age of roots; plants of the new *Begonia* have not been observed to form tubers.

*Rooting habit*.—Freely branching habit; dense.

Plant description:

*Plant and growth habit*.—Broadly upright and mounded plant habit; overall plant shape, globular to broadly obovate; moderately vigorous growth habit and moderate growth rate.

*Plant height, soil level to top of foliar plane*.—About 22.7 cm.

*Plant height, soil level to top of floral plane*.—About 25.3 cm.

*Plant width*.—About 31.4 cm.

*Lateral branch description*.—Branching habit: Freely branching habit with about three basal branches each with about three lateral branches developing per plant; pinching is not required. Length: About 10.8 cm. Diameter: About 1 cm. Internode length: About 2.6 cm. Strength: Moderately strong. Aspect: About 27.5° from vertical. Texture and luster: Sparsely pubescent; slightly glossy. Color, developing: Close to 144A. Color, fully developed: Close to 146B.

*Leaf description*.—Arrangement: Alternate, simple. Length: About 13.8 cm. Width: About 10.5 cm. Shape: Broadly ovate. Apex: Acute. Base: Oblique, lobes not imbricate. Margin: Dentate to crenate; moderately to strongly undulate. Texture and luster, upper surface: Sparsely pubescent; velvety; slightly glossy. Texture and luster, lower surface: Sparsely pubescent; velvety; moderately glossy. Venation pattern: Pinnate. Color: Developing leaves, upper surface: Close to between NN137A and 147A. Developing leaves, lower surface: Close to 148B. Fully expanded leaves, upper surface: Slightly darker than between NN137A and 147A; venation, close to 144A and distally, close to 181A. Fully expanded leaves, lower surface: Close to 148B slightly to moderately tinged with close to 181C; venation, close to 146C. Petioles: Length: About 5.2 cm. Diameter: About 5 mm. Strength: Moderately strong, flexible. Texture and luster, upper and lower surfaces: Moderately pubescent; slightly glossy. Color, upper and lower surfaces: Close to 144B; distally, close to 181A. Stipules: Quantity per leaf: Two. Length: About 9 mm. Width: About 8 mm. Shape: Deltoid. Apex: Bluntly acute. Base: Broadly cuneate. Margins: Entire, ciliate. Color, upper and lower surfaces: Close to 144B and 145A; towards the margins, close to 157D.

Flower description:

*Flowering habit*.—Rotate single-type male flowers arranged in axillary compound cymes; freely flowering habit with about nine flowers per cyme and about 175 flowers developing per plant during the flowering season; flowers face upright to outwardly.

*Fragrance*.—None detected.

*Natural flowering season*.—Long flowering period, plants flower freely and continuously from spring into the autumn in The Netherlands; during the winter in a greenhouse, plants begin flowering about five weeks after exposure to photoinductive treatments.

*Postproduction longevity*.—Individual flowers last about ten days on the plant; flowers not persistent; plants maintain good substance for about 20 to 30 days in an interior environment.

*Inflorescence height*.—About 11 cm.

*Inflorescence diameter*.—About 8.8 cm.

*Flower buds*.—Length: About 1.9 cm. Diameter, flattened: About 7 mm to 22 mm. Shape: Reniform; flattened. Texture and luster: Smooth, glabrous; velvety; matte. Color: Close to 179B; towards the apex and margins, close to 185C; at the base, tinged with close to N148B.

*Flowers*.—Diameter: About 5 cm. Depth: About 1.5 cm. Tepals: Quantity and arrangement: Four per flower arranged in two whorls. Length, lower tepals:

About 2.8 cm. Width, lower tepals: About 3 cm. Length, upper tepals: About 2.6 cm. Width, upper tepals: About 2.5 cm. Shape, lower tepals: Roughly reniform. Shape, upper tepals: Broadly obovate. Apex, lower and upper tepals: Rounded. Base, lower tepals: Broadly cuneate. Base, upper tepals: Cuneate. Margin, lower and upper tepals: Entire; slightly undulate. Texture and luster, lower and upper tepals, upper surface: Smooth, glabrous, velvety; matte. Texture and luster, lower and upper tepals, lower surface: Smooth, glabrous, velvety; matte and at the base, slightly glossy. Color, lower tepals: When opening, upper surface: Close to 70D; towards the apex and margins, close to 61D. When opening, lower surface: Close to 181C; towards the base, close to 160B. Fully opened, upper surface: Close to 63C; towards the apex and margins, close to 63B; at the margins, close to 53C to 53D; at the base, tinged with close to 145D; venation, close to 197C; color does not fade with development. Fully opened, lower surface: Close to 54B; towards the base, strongly tinged with close to 161C; venation, close to 182C; color does not fade with development. Color, upper tepals: When opening, upper surface: Close to 68C; towards the apex and margins, close to between N66C and 68A. When opening, lower surface: Close to 62B; towards the apex and margins, close to 64D. Fully opened, upper surface: Close to 62B to 62C; towards the apex and margins, close to 63C; venation, close to 197C; color does not fade with development. Fully opened, lower surface: Close to between 61D and 64C; towards the base, slightly tinged with close to 150D; venation, close to 182C; color does not fade with development. Tepaloids: Quantity and arrangement: If present, about 25 arranged in about five whorls at the center of the flower. Length, largest tepaloids: About 1.5 cm. Width, largest tepaloids: About 9 mm. Shape: Roughly obovate. Apex: Obtuse. Base: Cuneate. Margin: Entire; not undulate. Texture and luster, upper and lower surfaces: Smooth, glabrous, velvety; matte. Color: When opening, upper surface: Close to 68C; towards the apex and margins, close to between N66C and 68A. When opening, lower surface: Close to 62B; towards the apex and margins, close to 64D. Fully opened, upper surface: Close to 62B to 62C; towards the apex and margins, close to 63C; venation, close to 197C; color does not fade with development. Fully opened, lower surface: Close to between 61D and 64C; towards the base, slightly tinged with close to 150D; venation, close to 182C; color does not fade with development.

*Peduncles*.—Length: About 5.5 cm. Diameter: About 3 mm to 4 mm. Angle: About 30° from lateral branch axis. Strength: Moderately strong; flexible. Texture and luster: Sparsely pubescent; moderately glossy. Color: Close to 146B to 146C.

*Pedicels*.—Length: About 1.9 cm. Diameter: About 2 mm. Angle: About 30° from the peduncle axis. Strength: Moderately strong; flexible. Texture and luster: Moderately pubescent; moderately glossy. Color: Close to 199B.

*Flower bracts*.—Quantity and arrangement: Two per flower, opposite. Length: About 1 cm. Width: About 1.3 cm. Shape: Roughly reniform. Apex: Obtuse; ciliate. Base: Broadly cuneate. Margin: Entire; ciliate. Texture and luster, upper and lower surfaces: Smooth, glabrous; moderately glossy. Color, upper and lower surfaces: Close to 144A and 145A; margins, close to 157D.

*Reproductive organs*.—None observed, all structures transformed into tepaloids.

*Seeds and fruits*.—Seed and fruit development have not been observed on plants of the new *Begonia* as flowers are sterile.

Pathogen & pest resistance: Resistance to pathogens and pests common to *Begonia* plants has not been observed on plants of the new *Begonia*.

Temperature tolerance: Plants of the new *Begonia* have been observed to tolerate high temperatures of about 35° C. and to be suitable for USDA Hardiness Zones 10 to 12.

It is claimed:

1. A new and distinct *Begonia* plant named 'BKPBEMCRS' as illustrated and described.

* * * * *